United States Patent
Eppstein et al.

(10) Patent No.: US 6,530,915 B1
(45) Date of Patent: *Mar. 11, 2003

(54) PHOTOTHERMAL STRUCTURE FOR BIOMEDICAL APPLICATIONS, AND METHOD THEREFOR

(75) Inventors: Jonathan A. Eppstein, Atlanta, GA (US); Michael R. Hatch, Sugar Hill, GA (US); Difei Yang, Alpharetta, GA (US)

(73) Assignees: SpectRx, Inc., Norcross, GA (US); Altea Technologies, Inc., Tucker, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/622,427
(22) PCT Filed: Mar. 5, 1999
(86) PCT No.: PCT/US99/04929
§ 371 (c)(1),
(2), (4) Date: Oct. 20, 2000
(87) PCT Pub. No.: WO99/44638
PCT Pub. Date: Sep. 10, 1999

Related U.S. Application Data

(60) Provisional application No. 60/077,135, filed on Mar. 6, 1998.

(51) Int. Cl.⁷ ............................................... A61B 18/20
(52) U.S. Cl. .................................. 606/2; 606/9; 606/10; 606/13; 606/28; 607/89; 607/96; 600/309; 600/310; 600/316
(58) Field of Search .......................... 606/3, 9, 10, 132, 606/28; 607/88, 89, 96; 600/309, 310, 316

(56) References Cited

U.S. PATENT DOCUMENTS 5,885,211 A   3/1999   Eppstein et al.
6,142,939 A * 11/2000   Eppstein et al. ............... 607/96

FOREIGN PATENT DOCUMENTS

WO   WO 97/07734 A   3/1997

* cited by examiner

*Primary Examiner*—David M. Shay
(74) *Attorney, Agent, or Firm*—Needle & Rosenberg, P.C.

(57) ABSTRACT

A photothermal structure designed for the uniform application of a photothermal material, such as, for example, a dye or a pigment, to a tissue, e.g., the stratum corneum. In one embodiment, the photothermal structure comprises photothermal material combined with a carrier, such as, for example, an adhesive or an ink, and the resulting combination is applied to a substrate, such as, for example, an inert polymeric substrate to form a photothermal structure. In another embodiment, the photothermal structure comprises photothermal material incorporated into a film-forming polymeric material.

18 Claims, 2 Drawing Sheets

PHOTOTHERMAL STRUCTURE FOR BIOMEDICAL APPLICATIONS, AND METHOD THEREFOR

This application claims the priority benefit of U.S. Provisional Application No. 60/077,135 filed Mar. 6, 1998.

BACKGROUND OF THE INVENTION

1. Field of the Invention

This invention relates to a photothermal structure that is useful for the thermal ablation of tissue, such as for the creation of micropores.

2. Discussion of the Art

Traditional glucose monitoring devices operate on the principle of taking blood from an individual by a variety of methods, such as by needle or lancet. An individual applies a drop a blood to a strip which contains chemistry that interacts with the blood. The strip is inserted into a blood-glucose meter for measurement of glucose concentration based on a change in reflectance of the strip.

There are alternative glucose monitoring technologies being developed to provide a less invasive monitoring technique. One such technology involves measuring the level of glucose in interstitial fluid. In order to obtain samples of interstitial fluid, the barrier function of the stratum corneum must be overcome.

U.S. patent application Ser. No. 08/776,863 entitled "Microporation Of Human Skin For Drug Delivery and Monitoring Applications," filed Feb. 7, 1997, to Eppstein et al., discloses a method of ablating the stratum corneum to form at least one micropore by treating a selected area of the stratum corneum with an effective amount of an optical absorbing compound that exhibits strong absorption over the emission range of a light source and thermally ablating the stratum corneum by optically heating the optical absorbing compound. Heat is conductively transferred by the compound to the stratum corneum to elevate the temperature of tissue-bound water and other vaporizable substances in the selected area above the vaporization point of water and other vaporizable substances. This technique is hereinafter referred to as optical thermal ablation. Another microporation technique disclosed in that application involves the use of a solid thermal probe that is applied directly to the tissue. To the subject, these techniques are much less painful than using a lancet, if not completely painless.

In order to optimize the performance of the optical thermal ablation technique, it is desirable to accurately dispose a quantity of optical absorbing compound in contact with the tissue to be treated.

SUMMARY OF THE INVENTION

Briefly, the present invention is directed to a method and structure for the uniform application of a photothermal or photothermal material, such as, for example, a dye or a pigment, to a tissue, e.g., the stratum corneum, for the purpose of photothermal treatment of the tissue. In one embodiment, the photothermal structure comprises a photothermal material that is combined with a carrier, such as, for example, an adhesive or an ink, and the resulting combination is applied to a substrate, such as, for example, an inert polymeric substrate to form a photothermal structure. Means of application of the photothermal material to the carrier include, but are not limited to, printing, spraying, and casting. In another embodiment of a photothermal structure, the photothermal material may be incorporated into a film-forming polymeric material, and the resulting mixture can then be processed to form a film. The photothermal structure of either embodiment is placed in contact with the tissue, e.g., the stratum corneum, and illuminated with a light source, such as a laser.

The above and other objects and advantages of the present invention will become more readily apparent when reference is to made to the following description, taken in conjunction with the accompanying drawings.

DETAILED DESCRIPTION OF THE DRAWINGS

Definitions

Figure 1:
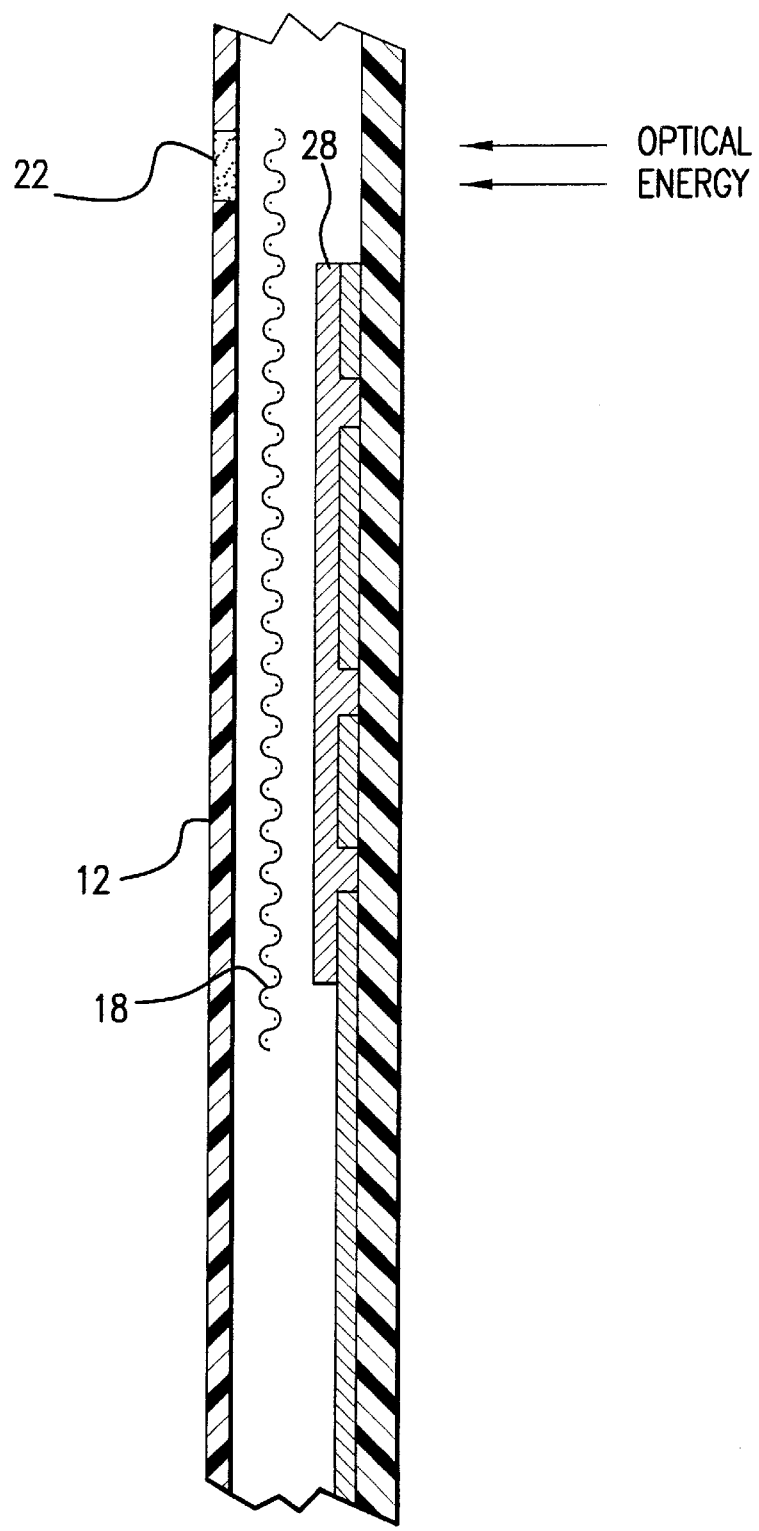
FIG. 1 is an enlarged longitudinal cross-sectional view of a device supporting a photothermal structure according to the present invention.

As used herein, the expression "biological fluid" is intended to include blood serum or whole blood as well as interstitial fluid. "Interstitial fluid" is the clear fluid that occupies the space between the cells in the body. The term "stratum corneum" means the outermost layer of the skin, consisting of from about 15 to about 20 layers of cells in various stages of drying out. The stratum corneum provides a barrier to the loss of water from inside the body to the external environment and from attack from the external environment to the interior of the body. The term "epidermis" means the metabolically active region of the skin. It is found just below the stratum corneum and is approximately 10 times as thick as the stratum corneum. The epidermis does not contain blood. The term "dermis" means the region of skin approximately 10 times as thick as the epidermis and found just below the epidermis. The dermis contains large amounts of collagen, which provides structural integrity to the skin. The dermis contains a layer of small blood capillaries that provide oxygen and nutrients to the rest of the layers of skin.

As used herein, the term "tissue" means an aggregate of cells of a particular kind, together with their intercellular substance, that form a structural material. At least one surface of the tissue must be accessible to electromagnetic radiation so that one embodiment of the invention can be carried out. The preferred tissue is the skin. Other tissues suitable for use with this invention include mucosal tissue and soft organs.

As used herein, "ablation" refers to the process of controlled removing a selected area of tissue from the surrounding tissue by kinetic energy released when vaporizable substances in the selected area is elevated above the vaporization point of water and other vaporizable substances thereby removing some of the tissue in the selected area.

As used herein, "poration," "microporation," or any such similar term means the formation of a small hole or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures.

As used herein, the expressions "photothermal material" means a compound or mixture of compounds that absorb electromagnetic radiation and radiate thermal energy and are capable of transferring thermal energy by conduction.

As used herein, the expressions "photothermal structure" or "photothermal assembly" means a structure comprising at least one layer containing a photothermal material. The structure may take the form of a film, sheet, block, membrane, gel, woven fabric, non-woven fabric, or combination of the foregoing. As used herein, the term "polymer" means a compound containing repeating structural units. The repeating structural units, i.e., monomers, include, but are not limited to, cellulosics, alkylene, ester, carbonate, amide, acrylic, agar, vinyl, and the like. As used herein, the term "adhesive" means a compound, or mixture of compounds, that promote adhesion between two surfaces.

As used herein, the term "integrated device" means a device suitable for microporating (when coupled to a suitable energy source) tissue, collecting a biological fluid from the tissue (preferably through the micropores so created) and analyzing the biological fluid to determine a characteristic thereof.

The term "heated probe" means a probe, preferably solid phase, which is capable of being heated in response to the application of electrical or electromagnetic (optical) energy thereto. For simplicity, the probe is referred to as a "heated probe" which includes a probe in a heated or unheated state, but which is heatable.

The microporation technique described herein is further described in co-pending U.S. application Ser. No. 08/776,863, filed Feb. 7, 1997, entitled "Microporation of Human Skin for Drug Delivery and Monitoring Applications," the entirety of which is incorporated herein by reference.

FIG. 1 illustrates an integrated tissue poration, fluid harvesting and analysis device, shown at reference numeral 10, that supports a photothermal structure according to the present invention. The device 10 comprises a tissue-contacting layer 12, which is designed to be placed in contact with tissue, such as skin, mucosal tissue, etc. The photothermal structure occupies a portion of the tissue-contacting layer 12, and is shown at reference numeral 22. An optional fluid-transporting layer 18 may be provided to transport biological fluid, such as interstitial fluid, by means of chemically aided wicking. A meter-interface layer 20 overlies the fluid-transporting layer 18 and supports a sensor 28 to contact the collected biological fluid for analysis.

Electromagnetic (e.g., optical) energy is projected through the meter-interface layer 20 onto the photothermal structure 22 on the tissue-contacting layer 12. Accordingly, the meter-interface layer 20 either has an opening 24 formed therethrough, or an entirety or sufficient portion of the meter-interface layer 20 is made of material transparent to electromagnetic energy at wavelengths used to heat the photothermal structure 22.

Further details about the device 10 are disclosed in U.S. Provisional Application No. 60/007,135, the entirety of which is incorporated herein by reference.

The photothermal structure 22 is capable of absorbing electromagnetic energy from a source, such as a laser or other optical source, to heat up and transfer the heat to the stratum corneum, forming a micropore in the skin, at a controlled and desired depth.

The photothermal structure 22 comprises a photothermal material provided in such a manner that it can be applied to tissue in a reproducible manner. This ensures that the quantity of photothermal material to which the tissue is exposed can be known accurately.

Photothermal materials suitable for use in this invention are capable of absorbing electromagnetic radiation at one or more wavelengths. Electromagnetic radiation considered to be suitable for this invention include radiation from the ultraviolet, visible and infrared regions of the electromagnetic spectrum. It is preferred, however, that visible radiation and infrared radiation be employed. Ultraviolet radiation has a wavelength ranging from about 10 nm to about 380 nm. Visible radiation has a wavelength ranging from about 380 nm to about 780 nm. Infrared radiation has a wavelength ranging from about 780 nm to about 50,000 nm. Photothermal materials suitable for use in this invention include, but are not limited to, dyes and pigments. The term "pigment" is used to describe the class of colorants that are practically insoluble in the media in which they are applied. Pigments retain a particulate form, suspended in the media. The term "dye" is used to describe colorants that are soluble, or at least partially soluble, in the media in which they are applied. Dyes exhibit an affinity to the substrate to which they are applied. Classes of dyes that are suitable for use in this invention include, but are not limited to, diphenyl-methane dyes, methin-polymethine dyes, porphine dyes, indathrene dyes, quinones, dithiol metal complexes, dioxazines, dithiazines, polymeric chromophores. Classes of pigments that are suitable for use in this invention include, but are not limited to, carbon black, carbon based pigments, metals, metal sols, dyed latexes, and inorganic pigments. Colorants that are preferred for this invention include copper phthalocyanine, indocyanine green, nigrosin, prussian blue, colloidal silver (20 to 100 nm diameter), carbon black, IR-780, IR-140, irgalan black, naphthol green B, tellurapyryllium, and vanadyl tetra-t-butyl-naphthalocyanine. In either case, particles of the dyes or pigments must be of a size that they can readily be blended with carrier materials. It is preferred that the particles of dyes and pigments have a major dimension, e.g., length, diameter, no greater than about 50 $\mu$m and preferably less than 5 $\mu$m.

The photothermal material preferably does not melt or decompose at temperatures below about 120° C, and is capable of absorbing an amount of electromagnetic energy and converting it to an amount of thermal energy sufficient to cause ablation of the tissue by the mechanism of conduction.

In one embodiment of this invention, the photothermal material is applied to the tissue-contacting layer 12 by means of a carrier. The tissue-contacting layer 12 serves as a substrate. The carrier is a material in which the photothermal material can be uniformly dissolved if the photothermal material is a dye, or uniformly suspended if the photothermal material is a pigment. Carrier materials suitable for use with dyes and pigments include, but are not limited to, solid polymers, adhesives, gels, liquids, glass, oils, greases and paper. These materials may comprise polymeric materials such as acrylics, silicones, polyesters, polycarbonates, polyimides, cellulosics, polyvinyl derivatives, polyethylene, polypropylene, and the like.

The concentration of photothermal material in the carrier can vary. A sufficient concentration of dye is typically that required to obtain an optical density greater than 1.0 at the wavelength of the laser. Determination of the appropriate concentration can readily be determined by trial-and-error by one of ordinary skill in the art.

In addition to the photothermal material, other ingredients that can be added to the carrier, but are not limited to, plasticizers, surfactants, binders, and crosslinking agents. These materials are commercially available.

In general, substrates to which the carrier containing the photothermal material can be applied (i.e., the tissue-contacting layer) include, but are not limited to, polymeric materials, cloth, non-woven materials, microporous membranes, glass, and metal foils. The substrate is preferably sufficiently flexible to allow close contact with the tissue. The substrate should adhere sufficiently to the carrier so that it does not detach before or during use. Materials that are suitable for preparing the substrate include, but are not limited to, polyesters, polyimides, polyethylenes, polypropylenes, polycarbonates, acrylics, cellulose, derivatives of cellulose, and the like.

In another embodiment, the photothermal material is blended with a film-forming material which forms the tissue-contacting layer 12. The film-forming material is preferably capable of being formed into a film that will allow uniform suspension of the photothermal material and will allow sufficient flexibility to conform to the tissue of the subject. Film-forming materials suitable for use in this embodiment include, but are not limited to, polyesters, polyimides, polyethylenes, polypropylenes, polycarbonates, acrylics, cellulose, derivatives of cellulose, and the like. Other substances can be combined into the suspension with the photothermal material, such as flux enhancer compounds that can be vaporized when the photothermal structure is heated, thereby being released into microporated tissue for acting on the tissue.

The thickness of the tissue-contacting layer 12 is not critical, but preferably ranges from about 0.05 mm to about 2.0 mm. The surface dimensions of this layer are not critical, but the major dimension preferably ranges from about 5 mm to about 60 mm and the minor dimension preferably ranges from about 5 mm to about 60 mm. The tissue-contacting layer 12 is shown as being rectangular, but other shapes are also suitable, e.g., circular, elliptical, triangular, square, and other shapes, and the same is true for the photothermal structure 22. The tissue-contacting layer 12 can be adhered to the skin of the subject by means of adhesive, electrostatic force, or pressure applied by the subject. The seal between the skin and the tissue-contacting layer 12 is preferably sufficiently tight so that biological fluid does not leak through or into it.

There are several ways to prepare the tissue-contacting layer 12 with the photothermal structure 22. According to one method, a pigment, e.g., carbon black, can be suspended uniformly into a pressure-sensitive adhesive composition. The adhesive composition can then be cast, or printed, onto a polymeric substrate. The adhesive composition can then be cured. According to another method, a dye, e.g., copper phthalocyanine, can be suspended in an organic solvent, e.g., ethanol. The suspension can be applied to one side of a polymeric membrane by means of an air-brush. The film can then be allowed to dry. According to still another method, a pigment, e.g., carbon black, can be suspended in a polymer based ink, such as clear nail polish. The ink can then be cast, or printed, onto a polymeric substrate. The film can then be cured. According to yet another method, a pigment, e.g., carbon black, can be blended into a polymeric material, e.g., linear low density polyethylene. The blend can then be melted and extruded into a film. The film can then be cured.

The photothermal structure has utility in many applications, including, but not limited to, the integrated device disclosed herein. The photothermal structure can be applied to the tissue in a variety of ways. In the case of the photothermal structure mixed with a carrier, the carrier can be a pressure-sensitive adhesive, which adheres the assembly to the tissue. In the case of the film, the film can be adhered to the tissue by means of electrostatic force. Other means of attachment include pressure applied to the film and vacuum to evacuate the area between the film or photothermal structure and the tissue to draw the film into contact with the tissue. Combinations of means of attachment can also be used.

The photothermal structure of the present invention overcomes several problems of the prior art, in particular in the manner of application. Specifically, pastes, or suspensions, of photothermal material have been applied topically to the target tissue. These materials have led to non-uniform and uncontrolled exposure to radiation from the laser. Variable and inaccurate application of the photothermal material can lead to unreproducible results of the photothermal treatment.

In addition, previous methods of applying a photosensitive dye to tissue give rise to difficulty in removing the excess dye following photothermal treatment. This difficulty also brings about the potential for contamination of adjacent tissue, clothing, etc., with residual dye.

The photothermal structure according to the present invention deploys photothermal material in such a manner that it can be readily removed from the tissue and discarded following photothermal treatment. Moreover, the photothermal structure deploys a photothermal material with reproducible results.

The following are examples of the photothermal structure.

EXAMPLE 1

Carbon black (20 nm) was suspended uniformly into an acrylic-based, pressure-sensitive adhesive (Aroset A 1081, Ashland Chemical) to provide a suspension having a concentration of 20 g carbon black/liter. The resulting suspension was cast onto a polyester film (25 $\mu$m thick). The adhesive was then cured by heating. After curing, the adhesive layer was approximately 50 $\mu$m thick. The combination of carbon black-adhesive and film substrate constituted the photothermal structure. A 0.4 inch diameter circle of the photothermal structure was prepared and placed on the volar forearm of the subject. Light from a 1 Watt, CW laser diode of 810 nm (Coherent Inc., Santa Clara Calif., part #S-81-100C-100T) was collimated and focused to a spot size of approximately 80 $\mu$m in diameter at the plane of the surface of the skin. At 250 mW peak power at the skin, 30 pulses of 50 msec each were delivered, each with 80 msec delays between pulses. The pulsing sequence was repeated to produce 6 photothermally treated sites spaced on the circumference of a 1.0 mm circle. After removal of the photothermal structure, the presence of the resulting small pores in the stratum corneum could be detected or observed.

EXAMPLE 2

Carbon black (<1 $\mu$m) was suspended into an acrylic-based ink, such as clear nail polish, to provide a suspension having a concentration of 10 g/l. The suspension was then cast, or printed, onto a polyester substrate (0.050 mm thick). The suspension was cured. The resulting coated substrate was then applied topically to the skin either directly, as a film, or, indirectly, as part of a device. Light from a laser or from a polychromatic light source was focused onto the film and interface between the colorant and the skin for the photothermal treatment. Following the photothermal treatment, the film was removed and discarded.

EXAMPLE 3

Carbon black (<1 $\mu$m) was blended into polyester to provide a blend having a final concentration of 10 g/l. The blend was commercially available under the trade designation "MELINEX 427/200." The blend was melted, and the melted blend was then extruded to form a film (0.050 mm thick). The film was then cured. The resulting film was then applied topically to the skin, either directly as a film or indirectly as part of a device. Light from a laser or from a polychromatic light source was focused onto the film and interface between the colorant and the skin for the photothermal treatment. Following the photothermal treatment, the film was removed and discarded.

EXAMPLE 4

Titanium metal was sputter-coated onto a polycarbonate film substrate. The substrate has a thickness of 2 mil (0.05 mm). The thickness of the titanium/titanium oxide layer was approximately 50 nm. The film was placed onto the skin, the metal layer being in contact with the skin. The film was maintained in proper position by an adhesive ring, which surrounded the targeted area. Light from a laser or from a polychromatic light source was focused onto the film and interface between the colorant and the skin for the photothermal treatment. Following the photothermal treatment, the film was removed and discarded.

The metal layer can be coated with a thin layer of polymeric material, such as 0.25 mil (0.006 mm) of polyoxymethylmethacrylate, as a protective layer.

EXAMPLE 5

The photothermal structure of Example 1 was placed onto the skin over the area to be treated. Light from a laser was focused onto the assembly to create a small region of thermally treated stratum corneum. The treated region was characterized by loss of adhesion of underlying cells. The region appears as a small pore surrounded by an area of loose skin, or an area resembling a small blister in which the cell adhesion in the epidermal layer has been disrupted. This treatment was repeated such that the individually treated areas overlap. When the adhesive was removed, the treated stratum corneum and some of the epidermis underlying the stratum corneum was removed. Remaining epidermis may be removed by mild abrasion with a sterile cotton swab. The treatment generally does not result in bleeding.

EXAMPLE 6

The method described in Example 5 was performed with an adhesive-free photothermal structure. Following photothermal treatment, the affected tissue was removed by mild rubbing with a cotton swab or by applying a sterile adhesive film, which can remove the tissue with the removal of the tape.

EXAMPLE 7

A small vacuum chamber having an orifice of 9 mm in diameter was placed over the skin, covering the 6 micropores, formed according to the procedures of Example 1. The chamber was evacuated to −6.00 psi for a period of two minutes. After the vacuum was released, the resulting clear fluid was collected by means of a micro-capillary tube. Volumes of 0.25 to 0.75 $\mu$l were routinely obtained through use of this protocol. The presence of fluid indicated that the photothermally generated pores had penetrated the stratum corneum into the underlying epidermis, breaching the barrier properties of the stratum corneum. No measurable fluid was obtained with application of the vacuum to untreated skin.

EXAMPLE 8

Samples of interstitial fluid were obtained as described in Example 7. The clear fluid was diluted into 1.0 ml of 5 mM phosphate, 0.02% sodium azide, pH 7.0. At the same time of sampling the interstitial fluid, blood plasma samples were obtained from the same subject. The finger of the subject was pierced with a lancet device, and blood was collected into a capillary tube containing heparin. The blood sample was centrifuged to separate the plasma fraction from the cellular fraction. A sample of 1.0 $\mu$l of plasma was transferred to 1.0 ml of phosphate buffer diluent by means of a micro capillary tube. The dilute samples of interstitial fluid and plasma were analyzed for glucose content by means of high pressure liquid chromatography with pulsed amperometric detection (HPLC-PAD). HPLC-PAD analysis was performed by using a Dionex PA-1 column, 4.0×250 mm, operated with a flow rate of 1.0 ml/min with 150 mM sodium hydroxide. Injection volumes of 10 $\mu$l were made. Glucose demonstrated a peak retention time of 4.0+0.3 minutes. Samples were compared to known aqueous and serum standards containing glucose, and concentrations were determined from the area of the glucose peak. The results contained from six healthy, non-diabetic subjects are set forth in the following table, where the units of glucose are mg/dl.

| Subject | Glucose in interstitial fluid | Glucose in plasma |
| --- | --- | --- |
| A | 102 | 116 |
| B | 123 | 143 |
| C | 147 | 123 |
| D | 113 | 120 |
| E | 88 | 94 |
| F | 102 | 105 |

EXAMPLE 9

To demonstrate the ability to deliver substances through the stratum corneum, sodium fluorescein was used as a model tracer. The volar forearm of a test subject was treated as in Example 1 to prepare a set of 6 pores comprising a circular pattern approximately 1.1 mm in diameter. Following poration, 1.0 $\mu$l of 10% sodium fluorescein in sterile saline was placed on the skin, covering the pores. A control area of skin, free of formed pores, was similarly covered with 1.0 $\mu$l of sodium fluorescein solution. After two minutes, the excess solution was removed by blotting, followed by washing with mild detergent, rinsing, and blotting dry. Where pores were formed, the skin demonstrated visible pigmentation due to the presence of fluorescein within the tissue. The area of yellow staining was approximately 1.4 mm in diameter. No staining was apparent for the control area. Under ultraviolet illumination, the area of the skin where pores were formed demonstrated intense yellow-green fluorescence covering an area of approximately 1.5 mm in diameter, due to the presence of the sodium fluorescein. The immediate area which outlined each of the six pores was more intensely fluorescent. In addition, there was a light fluorescence covering an area of approximately 2.0 mm in diameter which appeared to be due to some residual fluorescence in the outer stratum corneum.

Figure 2:
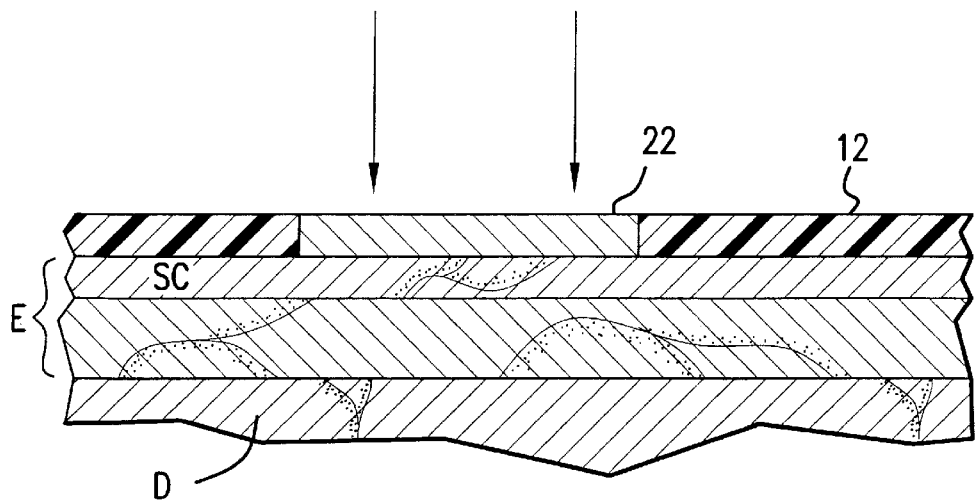
FIGS. 2 and 3 illustrate the use of the photothermal structure according to the present invention.
Figure 3:
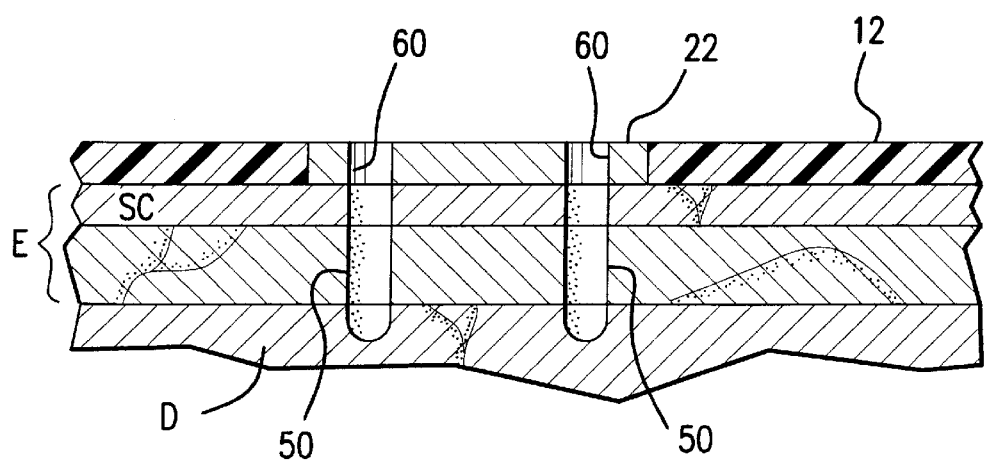

FIGS. 2 and 3 illustrate the operation and use of the photothermal structure. The photothermal structure can be used to form a micropore in the stratum corneum. Generation of small pores in the stratum corneum may be used to gain access to body fluids for diagnostic applications. Additionally, poration may be used to increase the permeability of some drugs or other bioactive agents. The photothermal structure according to the present invention may also be applied in surgical applications such as the treatment of surface lesions, tattoos, or other photothermal treatments of tissue surfaces.

In operation, the photothermal structure is placed against a surface of the tissue, such as skin, as shown in FIG. 2. A source of electromagnetic energy, such as optical energy, is activated and the energy is focused on the photothermal structure. After an appropriate period of time, e.g., from about 10 ms to about 1 second, the energy heats the photothermal structure 22, and the thermal energy in the photothermal structure 22 is transferred to the tissue to ablate the tissue and form at least one micropore 50 as shown in FIG. 3. In the example of FIG. 3, two micropores 50 are formed in the stratum corneum ("SC"), and the micropores may go as deep as through the epidermis ("E") and into the dermis ("D"). At the locations on the photothermal structure where the optical energy is focused, the photothermal structure melts or is burned so that small holes 60 are created. Biological fluid traverses the stratum corneum through the micropore 50 can be collected for analysis. For example, when the photothermal structure is employed in an integrated device such as that shown in FIG. 1, the biological fluid is collected and analyzed by the same apparatus that forms the micropores.

Sources of electromagnetic energy that are suitable for use with the photothermal structure according to the present invention are disclosed in U.S. patent application Ser. No. 08/776,863.

In summary, the photothermal structure, in one embodiment, comprises a quantity of photothermal material; a carrier which is combined with the photothermal material such that the photothermal material is substantially uniformly dissolved or suspended therein; and a substrate to which the carrier-photothermal material combination is applied. A layer of priming material may be provided between the substrate and the carrier. In another embodiment, the photothermal structure comprises a quantity of photothermal material; and a film material containing a substantially uniform suspension of the photothermal material.

Further, a method for treating tissue is provided, which comprises the steps of applying a photothermal structure including a quantity of photothermal material to tissue, and subjecting the photothermal structure to electromagnetic radiation. The step of applying may comprise applying a substrate, to which is applied a carrier incorporating a substantially uniform suspension of the photothermal material. The substrate may be adhered to the tissue. Alternatively, the step of applying may involve applying a film incorporating a substantially uniform suspension of the photothermal material.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A photothermal structure for treating tissue, comprising:
   (a) a quantity of photothermal material; and
   (b) a film material containing a substantially uniform suspension of the photothermal material.

2. The photothermal structure of claim 1, and wherein the film material is made of one of polyesters, polyimides, polyethylenes, polypropylenes, acrylics, cellulose and derivatives thereof.

3. The photothermal structure of claim 2, wherein the photothermal material is a dye or pigment.

4. A photothermal structure for treating tissue, comprising:
   (a) a quantity of photothermal material;
   (b) a carrier which is combined with the photothermal material such that the photothermal material is substantially uniformly dissolved or suspended therein; and
   (c) a substrate to which the carrier-photothermal material combination is applied.

5. The photothermal structure of claim 1, and further comprising a layer of priming material between the substrate and the carrier.

6. The photothermal structure of claim 1, wherein the photothermal material is a dye or a pigment.

7. The photothermal structure of claim 1, wherein the carrier is one of a solid polymer, adhesive, gel and ink.

8. A method for treating tissue comprising the steps of:
   (a) applying a photothermal structure including a quantity of photothermal material to the tissue; and
   (b) subjecting said photothermal structure to electromagnetic radiation.

9. The method of claim 8, wherein the step of applying comprises applying a film incorporating a substantially uniform suspension of the photothermal material.

10. The method of claim 8, wherein the electromagnetic radiation is in a wavelength range from about 10 nm to about 50,000 nm.

11. The method of claim 8, wherein said step of subjecting comprises emitting electromagnetic radiation from a polychromatic light source.

12. The method of claim 8, wherein said step of subjecting comprises emitting electromagnetic radiation from a laser.

13. The method of claim 8, and further comprising the step of introducing a permeant into said opening.

14. The method of claim 8, wherein the step of applying comprises applying a substrate to which is applied a carrier in which the quantity of photothermal material is substantially uniformly dissolved or suspended.

15. The method of claim 14, wherein the step of applying comprises adhering the substrate to the tissue.

16. The method of claim 8, and further comprising the step of withdrawing body fluids from an opening created by thermal ablation of the tissue.

17. The method of claim 16, and further comprising the step of determining the concentration of at least one analyte in the body fluids.

18. The method of claim 17, wherein the step of determining comprises determining the concentration of glucose.

* * * * *